United States Patent
Röder et al.

(10) Patent No.: US 10,876,226 B2
(45) Date of Patent: *Dec. 29, 2020

(54) POLYSACCHARIDE FIBERS AND METHOD FOR PRODUCING SAME

(71) Applicant: DUPONT INDUSTRIAL BIOSCIENCES USA, LLC, Wilmington, DE (US)

(72) Inventors: Thomas Röder, Vöcklabruck (AT); Gernot Kaindl, Lenzing (AT); Sigrid Redlinger, Lenzing (AT); Heinrich Firgo, Vöcklabruck (AT); Gert Kroner, Seewalchen (AT)

(73) Assignee: DUPONT INDUSTRIAL BIOSCIENCES USA, LLC, Wilmington, DE (US)

( * ) Notice: Subject to any disclaimer, the term of this patent is extended or adjusted under 35 U.S.C. 154(b) by 171 days.

This patent is subject to a terminal disclaimer.

(21) Appl. No.: 15/988,401

(22) Filed: May 24, 2018

(65) Prior Publication Data

US 2018/0340270 A1 Nov. 29, 2018

Related U.S. Application Data

(63) Continuation of application No. 14/899,212, filed as application No. PCT/AT2014/000124 on Jun. 13, 2014, now abandoned.

(30) Foreign Application Priority Data

Jun. 17, 2013 (AT) .................................. A 484-2013

(51) Int. Cl.
| | |
|---|---|
| *D01F 2/06* | (2006.01) |
| *C08B 37/00* | (2006.01) |
| *C08L 5/00* | (2006.01) |
| *D21H 13/08* | (2006.01) |
| *D01D 5/06* | (2006.01) |
| *C08L 1/02* | (2006.01) |
| *D04H 1/4258* | (2012.01) |
| *D04H 3/013* | (2012.01) |
| *D01F 9/00* | (2006.01) |
| *A61L 15/28* | (2006.01) |

(52) U.S. Cl.
CPC ................ *D01F 2/06* (2013.01); *A61L 15/28* (2013.01); *C08B 37/0009* (2013.01); *C08L 1/02* (2013.01); *C08L 5/00* (2013.01); *D01D 5/06* (2013.01); *D01F 9/00* (2013.01); *D04H 1/4258* (2013.01); *D04H 3/013* (2013.01); *D21H 13/08* (2013.01)

(58) Field of Classification Search
CPC .......... D21H 13/02; D21H 13/08; D01F 2/02; D01F 2/06; D01F 2/08; C08L 1/02; C08L 1/24; C08L 5/02; C08B 37/0009; C08B 37/0021; D01D 5/06
USPC ....... 162/157.7; 264/188, 189, 178 F, 178 R, 264/205, 207; 536/123.1, 123.12
See application file for complete search history.

(56) References Cited

U.S. PATENT DOCUMENTS

| | | | | |
|---|---|---|---|---|
| 2,914,414 | A * | 11/1959 | Novak | ....................... C08L 1/24 106/162.6 |
| 10,220,111 | B2 * | 3/2019 | Roder | .................. D04H 1/4258 |
| 2013/0313737 | A1 * | 11/2013 | O'Brien | .................... D01F 9/00 264/13 |

OTHER PUBLICATIONS

Caligur, V., "Dextran and Related Polysaccharides", BioFiles 2008, 3.10, 17. (Year: 2008).*

* cited by examiner

Primary Examiner — Eric Hug

(57) ABSTRACT

The present invention relates to a method for the production of polysaccharide fibers which contain a mixture of cellulose and α(1→3)-glucan as a fiber-forming substance, as well as to the fibers made thereby, and to their use.

13 Claims, 1 Drawing Sheet

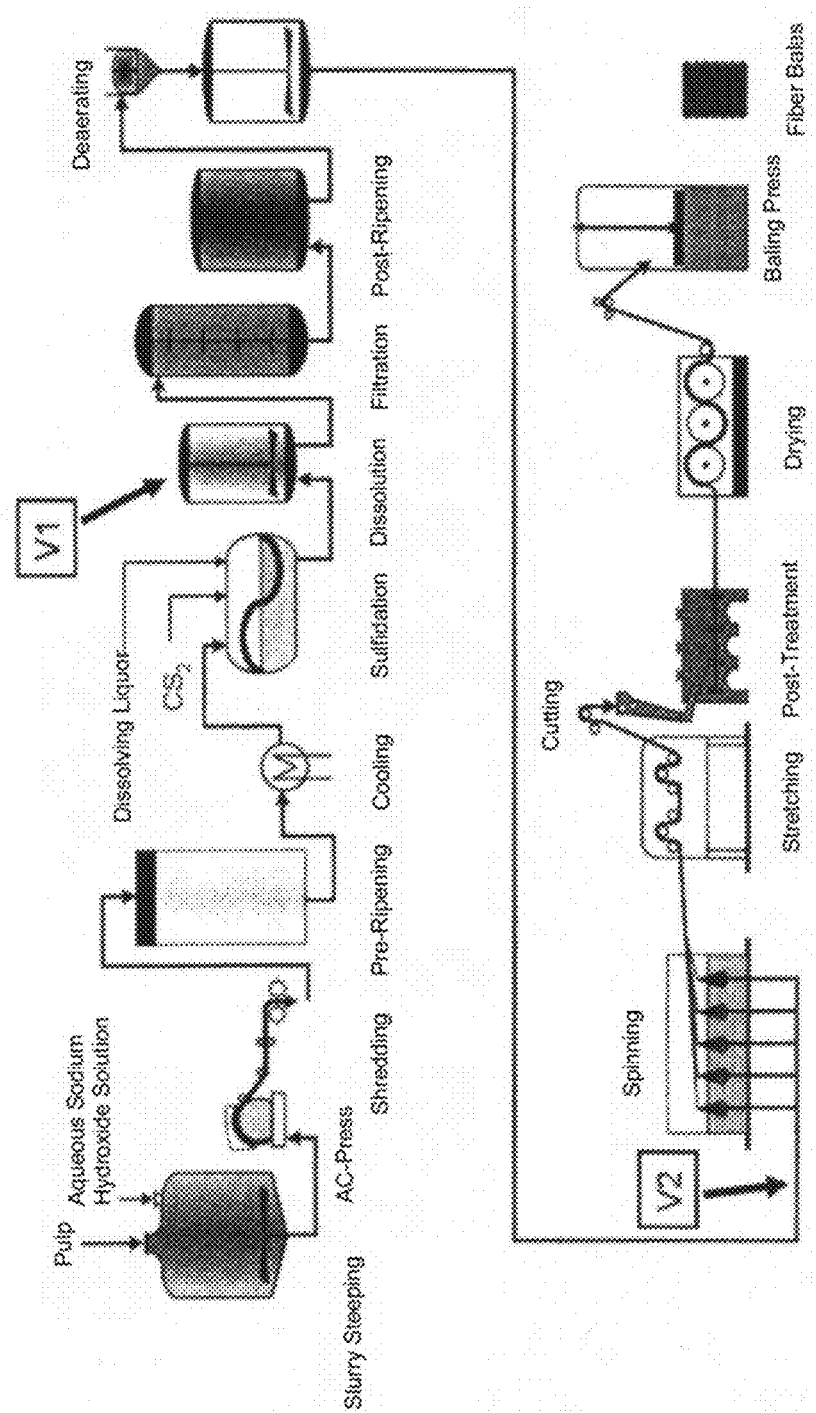

POLYSACCHARIDE FIBERS AND METHOD FOR PRODUCING SAME

The present application is a continuation of U.S. patent application Ser. No. 14/899,212, filed Dec. 17, 2015, published as U.S. 2016-0138196 A1, which is a national-stage entry under 35 U.S.C. § 371 of International Patent Application No. PCT/AT2014/000124, filed Jun. 13, 2014, published as WO 2014/201483 A1, which claims priority to Austrian Patent Application No. A 484-2013, filed Jun. 17, 2013, the entire disclosure of each of which is incorporated by reference herein.

BACKGROUND OF THE INVENTION

Field of the Invention

The present invention relates to a method for the production of polysaccharide fibers which contain a mixture of cellulose and $\alpha(1\to3)$-glucan as a fiber-forming substance, as well as to the fibers made thereby, and to their use.

Background of the Invention

Polysaccharides are becoming increasingly important, as they are materials that can be obtained from renewable raw materials. One of the most frequently occurring polysaccharides is cellulose. Cotton fibers, which consist almost exclusively of cellulose, are an example of the significance of polysaccharides. However, also materials obtained from other cellulosic raw materials, e.g., cellulosic synthetic fibers, are continuing to gain in importance.

The generic names "viscose fibers" and "modal fibers" were assigned by BISFA (the International Bureau for the Standardization of Man-made Fibers) to cellulose fibers produced through chemical derivatization of cellulose with the help of aqueous sodium hydroxide solution and carbon disulfide.

The name "modal fiber" is a generic term which, as defined by BISFA, stands for a cellulose fiber having a defined high wet strength and an also defined high wet modulus (i.e., the force required to produce an elongation of the fiber of 5% in its wet state). The modal process can be regarded as a variation of the viscose process.

For the purposes of the present invention, viscose and modal processes shall be referred to collectively as "xanthogenate processes", as in them polysaccharides are always reacted with $CS_2$ into the respective xanthogenates. Xanthogenate processes for the production of cellulose fibers have generally been known to those skilled in the art for decades. A method for the production of modal fibers is, for example, known from AT 287.905 B.

The cellulosic raw material that is primarily used in xanthogenate processes is pulp obtained from wood. The cellulose molecules that exist in wood and also in other plant-based sources of cellulose such as cotton linters, straw, etc. form very long chains, i.e., they exhibit a high degree of polymerization. In order to obtain a cellulose spinning solution that is well suited for large-scale processing, it is necessary to specifically adjust the degree of polymerization of the cellulose molecules, which inevitably causes a part of the polymer molecules to be shortened. This takes place in the usual pulp preparation procedures and also in separate pretreatment steps such as bleaching, acid treatment, or irradiation by splitting of the originally long cellulose molecules. In addition to the shorter chains having the desired degree of polymerization, this also creates significantly shorter fragments such as oligomers or even monomers which remain in solution after the precipitation of the spinning solution in the precipitation bath, do not contribute to the formation of the fibers, and thus are lost. The quantities of raw material lost in this process can be substantial and can affect the cost-effectiveness of the entire process.

U.S. Pat. No. 7,000,000 describes fibers obtained by spinning a solution of polysaccharides which substantially consist of repeating hexose units linked via $\alpha(1\to3)$-glycosidic bonds. These polysaccharides can be produced by bringing an aqueous solution of saccharose into contact with glucosyltransferase (GtfJ), isolated from *Streptococcus salivarius* (Simpson et al., Microbiology, vol. 41, pp 1451-1460 (1995)). As used in this context, "substantially" means that within the polysaccharide chains there may exist occasional defective locations where other bond configurations may occur. For the purposes of the present invention, these polysaccharides shall be referred to as "$\alpha(1\to3)$-glucan".

U.S. Pat. No. 7,000,000 first discloses possibilities for the enzymatic production of $\alpha(1\to3)$-glucan from monosaccharides. In this way, relatively short-chained polysaccharides can be produced without the loss of monomer units, as the polymer chains are built from the monomer units. Contrary to the production of short-chained cellulose molecules, the production of $\alpha(1\to3)$-glucan keeps getting less expensive the shorter the polymer chains are, as in that case only a short residence time in the reactors will be required.

According to U.S. Pat. No. 7,000,000, the $\alpha(1\to3)$-glucan is to be derivatized, preferably acetylated. Preferably, the solvent is an organic acid, an organic halogen compound, a fluorinated alcohol, or a mixture of such components. These solvents are costly and complex to regenerate.

It was therefore attempted to use $\alpha(1\to3)$-glucans instead of cellulose in a viscose or modal process under large-scale commercially applied process conditions. Unfortunately, it was found that in these conditions $\alpha(1\to3)$-glucans could not be processed satisfactorily into fibers, as glucans dissolve in a diluted aqueous sodium hydroxide solution. In view of this fact, it is not possible to simply use $\alpha(1\to3)$-glucans instead of cellulose in the existing methods.

Object

In view of such prior art, the object was therefore to provide a polysaccharide fiber as well as a method for the production thereof which does not include the above mentioned problems (e.g., of solubility in an aqueous sodium hydroxide solution). The polysaccharide raw material was to be inexpensive, and the processing method should have already been confirmed as suitable for large-scale use and was to be cost-effective and executable on existing facilities.

BRIEF DESCRIPTIONS OF THE DRAWINGS

FIG. 1 is a schematic depicting the production process for a fiber made in accordance with the present invention.

DESCRIPTION OF THE INVENTION

The above described object is solved by a method for the production of a polysaccharide fiber using a xanthogenate process, wherein the fiber-forming substance is a mixture of cellulose and $\alpha(1\to3)$-glucan. The $\alpha(1\to3)$-glucan can be added at various locations of the process in the form of an $\alpha(1\to3)$-glucan-containing aqueous sodium hydroxide solution. For the purposes of the present invention, a fiber produced in this way shall also be referred to as viscose or modal fiber even though, in addition to cellulose, it also contains another fiber-forming polysaccharide, namely, said α(1→3)-glucan.

For the purposes of the present invention, the term "fiber" shall comprise both staple fibers having a defined staple length and continuous filaments. All principles of the invention that are described hereinafter generally apply to both staple fibers and continuous filaments.

The single fiber titer of the inventive fibers can be between 0.1 and 10 dtex. Preferably, it is between 0.5 and 6.5 dtex, and more preferably between 0.9 and 6.0 dtex. In the case of staple fibers, the staple length is usually between 0.5 and 120 mm, preferably between 20 and 70 mm, and more preferably between 35 and 60 mm. In the case of continuous filaments, the number of individual filaments in the filament yarn is between 50 and 10,000, preferably between 50 and 3,000.

The α(1→3)-glucan can be prepared by bringing an aqueous solution of saccharose into contact with glucosyltransferase (GtfJ) isolated from *Streptococcus salivarius* (Simpson et al., Microbiology, vol. 41, pp 1451-1460 (1995)).

Preferred embodiments of the inventive method are the variants of the viscose process generally known to those skilled in the art as well as of a viscose process modified for the production of modal fibers.

In a preferred embodiment of the method according to the invention, at least 90% of the α(1→3)-glucan are hexose units and at least 50% of the hexose units are linked via α(1→3)-glycosidic bonds.

The method for the production of the inventive fiber consists of the following steps (also see FIG. 1):

1. Preparing the alkali cellulose, and its xanthogenation;
2a. Adding α(1→3)-glucan together with the dissolving liquor (FIG. 1, addition location V1), preferably by addition into an appropriate agitating vessel;
or
2b. Dissolving the xanthogenate in dissolving liquor and addition of α(1→3)-glucan in alkaline solution between the dissolver and the spinning machine (FIG. 1, addition location V2), preferably by an appropriate inline mixing unit known to those skilled in the art;
3. Extruding the α(1→3)-glucan-containing spinning solution through a spinneret into a sulfuric acid spin bath, stretching the fibers, and post-treatment.

The concentration of the fiber-forming substance in the spinning solution can be between 4 and 15% by weight, preferably it is between 5.5 and 12% by weight.

In the inventive method, the fiber-forming substance can contain between 1 and 99% by weight of α(1→3)-glucan. Preferred is a content of the α(1→3)-glucan between 5 and 45% by weight. Below 5% by weight of α(1→3)-glucan, the economic benefit of the added α(1→3)-glucan is too low for typical types of use of the inventive fibers; above 45%, competing reactions for the $CS_2$ in the spinning solution become too intensive, and the spinnability of the solution decreases significantly. However, under certain conditions and/or for certain types of use of the inventive fibers, both limits may be exceeded; the scope of the present invention expressly also includes fibers having an α(1→3)-glucan content between 1 and 5% by weight and between 45 and 99% by weight, respectively.

Preferably, the remaining part of the fiber-forming substance consists substantially of cellulose. As used in this context, "substantially" means that low quantities of other substances can be present which primarily originate from the cellulosic raw material, generally from said pulp. Such other substances include primarily hemicellulose and other saccharides, lignin residues, or the like. They are also contained in commercially available viscose and modal fibers.

However, the scope of the present invention shall expressly also include such fibers that, in addition to the constituents mentioned so far, also contain other polysaccharides or functional additives as generally known in the nonwoven and textile industries.

The degree of polymerization of the α(1→3) glucan employed in the method according to the invention, expressed as weight average $DP_w$, can be between 200 and 2000; values between 500 and 1000 are preferred.

A polysaccharide fiber produced by using a xanthogenate process and containing cellulose and α(1→3)-glucan as fiber-forming substances is also the subject-matter of the present invention. Preferably, the fiber-forming substance contains between 1 and 99% by weight of α(1→3)-glucan and more preferably between 5 and 45% by weight of α(1→3)-glucan.

In a preferred embodiment, at least 90% of the α(1→3)-glucan of the inventive polysaccharide fiber are hexose units and at least 50% of the hexose units are linked via α(1→3)-glycosidic bonds.

The use of the inventive fibers for the production of various dry-laid and wet-laid papers, nonwovens, hygiene articles such as tampons, panty liners, and diapers, and other nonwovens, especially absorbent nonwoven products, but also of textile products such as yarns, woven fabrics, or knitted fabrics is also the subject-matter of the present invention.

The invention will be described below with reference to examples. However, the invention is not expressly limited to these examples but also includes all other embodiments that are based on the same inventive concept.

EXAMPLES

The degree of polymerization of the α(1→3)-glucans was determined by means of GPC in DMAc/LiCl. Subsequently, it is always the weight average of the degree of polymerization ($DP_w$) that is specified.

Example 1

A viscose xanthogenate containing 29.8% by weight of cellulose, 14.9% by weight of alkali, and 8% by weight of sulfur was reacted in a dissolving unit with a first dissolving liquor containing 4.5% by weight of NaOH and then with a second dissolving liquor containing 9% by weight of α(1→3)-glucan and 4.5% by weight of NaOH and finally with water. The viscose obtained in this way contains 9% by weight of fiber-forming material, 5.20% by weight of alkali, and 2.4% by weight of sulfur (calculated under the assumption that there are 100% by weight of cellulose as a fiber-forming material), with a ripeness index of 14 Hottenroth and a falling ball viscosity of 80 seconds (determined according to the Zellcheming Leaflet III/5/E). Viscose solutions with 10 and 25% of α(1→3)-glucan were prepared. These glucan quantities were related to the proportion of the α(1→3)-glucan in the fiber-forming substance. These viscose types contain 2.2% by weight of sulfur (10% by weight of glucan and 90% by weight of cellulose as fiber-forming materials) and 1.8% by weight of sulfur (25% by weight of glucan and 75% by weight of cellulose as fiber-forming materials), respectively. By using a spinneret, the solution was extruded into a regeneration bath containing 100 g/l of sulfuric acid, 330 g/l of sodium sulfate, and 15 g/l of zinc sulfate. The spinneret had 1053 perforations with a diameter of 50 μm. 0.5% by weight of a nitrogen-containing auxiliary agent were added to the viscose spinning solution. In order to achieve adequate fiber strength, stretching by approx. 75% was carried out in the second bath (92° C., 15 g/l of $H_2SO_4$). The draw-off velocity was 50 m/min.

In a reference example 1, the viscose from Example 1 was spun into fibers without the addition of the glucan/NaOH solution, but otherwise in the same conditions as in Example 1.

The properties of the obtained fibers are listed in Table 1.

Example 2

A viscose containing 8.70% by weight of cellulose, 5.20% by weight of alkali, and 2.3% by weight of sulfur, with a ripeness index of 15 Hottenroth and a falling ball viscosity of 75 seconds (determined according to the Zellcheming Leaflet III/5/E), was, by means of a spinneret, extruded into a regeneration bath containing 100 g/l of sulfuric acid, 310 g/l of sodium sulfate, and 15 g/l of zinc sulfate. The spinneret had 1053 perforations with a diameter of 50 μm. 0.5% by weight of a nitrogen-containing auxiliary agent were added to the viscose spinning solution. In order to achieve adequate fiber strength, stretching by approx. 75% was carried out in the second bath (92° C., 15 g/l of $H_2SO_4$). The draw-off velocity was 50 m/min.

By using a positive displacement pump, various weight/weight percentages of a α(1→3)-glucan solution (prepared with 5% by weight of NaOH, 8% by weight of α(1→3)-glucan) were added to the viscose solution upstream from the spinneret, and fibers having 5, 10, 15, and 30% of glucan were produced (FIG. 1, V2). These glucan quantities were related to the mass fraction of the α(1→3)-glucan in the fiber-forming substance.

In a reference example 2, the viscose from Example 2 was spun into fibers without the addition of the glucan/NaOH solution, but otherwise in the same conditions as in Example 2.

The properties of the obtained fibers are listed in Table 1.

Example 3

A modal viscose containing 6.0% by weight of cellulose, 6.20% by weight of alkali, and 1.8% by weight of sulfur, with a gamma value of 65 and a falling ball viscosity of 130 seconds (determined according to the Zellcheming Leaflet III/5/E) was, by means of a spinneret, extruded into a regeneration bath containing 72 g/l of sulfuric acid, 115 g/l of sodium sulfate, and 55 g/l of zinc sulfate. The spinneret had 1053 perforations with a diameter of 45 μm. 2.5% by weight of a nitrogen-containing auxiliary agent were added to the viscose spinning solution. In order to achieve adequate fiber strength, stretching by approx. 115% was carried out in the second bath (92° C., 15 g/l of $H_2SO_4$). The draw-off velocity was 50 m/min.

By using a positive displacement pump, various weight/weight percentages of a α(1→3)-glucan solution (prepared with 5% by weight of NaOH, 4.5% by weight of α(1→3)-glucan) were added to the viscose solution upstream from the spinneret, and fibers having 5 and 15% of glucan were produced. These glucan quantities were related to the mass fraction of the α(1→3)-glucan in the fiber-forming substance.

In a reference example 3, the viscose from Example 3 was spun into fibers without the addition of the glucan/NaOH solution, but otherwise in the same conditions as in Example 3.

The properties of the obtained fibers are listed in Table 1.

TABLE 1

| example | additive | quantity of glucan % | titer dtex | FFk cN/tex | FDk % | FFn cN/tex | FDn % |
|---|---|---|---|---|---|---|---|
| reference example 1 | none | — | 1.7 | 27.4 | 16.2 | 15.7 | 16.8 |
| 1a | glucan $DP_W 800$ | 10 | 1.7 | 27.4 | 16.5 | 15.0 | 17.1 |
| 1b | glucan $DP_W 800$ | 25 | 1.7 | 21.9 | 14.2 | 12.0 | 16.3 |
| reference example 2 | none | — | 1.3 | 29.6 | 15.8 | 17.4 | 16.6 |
| 2a | glucan $DP_W 800$ | 5 | 1.3 | 29.2 | 16.1 | 16.0 | 17.7 |
| 2b | glucan $DP_W 800$ | 10 | 1.3 | 28.6 | 17.9 | 14.9 | 21.1 |
| 2c | glucan $DP_W 800$ | 15 | 1.3 | 26.1 | 18.1 | 12.7 | 21.1 |
| 2c | glucan $DP_W 800$ | 30 | 1.3 | 23.6 | 19.4 | 12.1 | 20.1 |
| reference example 3 | none | — | 1.3 | 38.8 | 12.6 | 22.7 | 13.0 |
| 3a | glucan $DP_W 1000$ | 5 | 1.3 | 37.6 | 13.3 | 22.1 | 14.3 |
| 3b | glucan $DP_W 1000$ | 15 | 1.3 | 36.2 | 13.4 | 20.3 | 13.9 |

FFk fiber strength, conditioned
FDk fiber elongation, conditioned
FFn fiber strength, wet
FDn fiber elongation, wet

What is claimed is:

1. A method of producing a polysaccharide fiber comprising cellulose and α(1→3)-glucan, said method comprising:
   (i) preparing an alkaline cellulose xanthogenate composition;
   (ii) combining the alkaline cellulose xanthogenate composition with a composition comprising α(1→3)-glucan to provide a spinning solution that comprises a fiber-forming substance, wherein substantially all of the glycosidic bonds of the α(1→3)-glucan are α(1→3)-glycosidic bonds, and wherein the fiber-forming substance comprises 5% to 45% by weight the α(1→3)-glucan; and
   (iii) extruding the spinning solution to produce the polysaccharide fiber.

2. The method of claim 1, wherein the polysaccharide fiber is a modal fiber.

3. The method of claim 1, wherein the polysaccharide fiber is a staple fiber or a continuous filament.

4. A polysaccharide fiber produced according to the method of claim 1.

5. The polysaccharide fiber of claim 4, wherein the polysaccharide fiber is a staple fiber or a continuous filament.

6. A textile product comprising the polysaccharide fiber of claim 4, wherein the textile product is selected from the group consisting of yarns, woven fabrics, and knitted fabrics.

7. A product comprising the polysaccharide fiber of claim 4, wherein the product is a nonwoven, hygiene article, or paper.

8. The textile product of claim 6, wherein the polysaccharide fiber is a staple fiber or a continuous filament.

9. The product of claim 7, wherein the product is said hygiene article, wherein the hygiene article is selected from the group consisting of tampons, panty liners, and diapers.

10. The product of claim 7, wherein the polysaccharide fiber is a staple fiber or a continuous filament.

11. The method of claim 1, further comprising (iv) stretching the polysaccharide fiber.

12. The method of claim 1, wherein the weight-average degree of polymerization (DPw) of the α(1→3)-glucan is between 200 and 2000.

13. The method of claim 12, wherein the DPw of the α(1→3)-glucan is between 500 and 1000.

* * * * *